(12) United States Patent
Bruder et al.

(10) Patent No.: US 9,642,740 B2
(45) Date of Patent: *May 9, 2017

(54) MOIST HEAT THERAPY COMPRESS

(71) Applicant: BRUDER HEALTHCARE COMPANY, Alpharetta, GA (US)

(72) Inventors: Mark H. Bruder, Alpharetta, GA (US); Aaron N. Ingram, Canton, GA (US)

(73) Assignee: BRUDER HEALTHCARE COMPANY, LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/560,998

(22) Filed: Dec. 4, 2014

(65) Prior Publication Data

US 2015/0088236 A1    Mar. 26, 2015

Related U.S. Application Data

(63) Continuation of application No. 13/832,626, filed on Mar. 15, 2013, now Pat. No. 9,445,939, which is a
(Continued)

(51) Int. Cl.
*A61F 7/02*    (2006.01)
*A61F 13/00*    (2006.01)
(Continued)

(52) U.S. Cl.
CPC .......... *A61F 7/02* (2013.01); *A61F 13/00021* (2013.01); *A61F 13/00063* (2013.01);
(Continued)

(58) Field of Classification Search
CPC .............. A61F 7/02; A61F 2013/00187; A61F 13/00021; A61L 2300/104;
(Continued)

(56) References Cited

U.S. PATENT DOCUMENTS 2,066,271 A    12/1936  Irwin
2,882,244 A    4/1959   Milton
(Continued)

FOREIGN PATENT DOCUMENTS

EP    0099748    5/1987
EP    0230387    4/1988
(Continued)

OTHER PUBLICATIONS

Encylopedia Britannica, bentonite definition.*
(Continued)

*Primary Examiner* — Kim M Lewis
(74) *Attorney, Agent, or Firm* — Gardner Groff Greenwald & Villanueva, PC

(57) ABSTRACT

A moist heat therapy compress for therapeutic treatment of a treated body part. The moist heat therapy compress includes a fluid-permeable shell, a flexible backing fastened to the shell to define an enclosure, and hydrophilic zeolite fill granules loosely contained within the enclosure. The moist heat therapy compress is exposed to a source of moisture to cause absorption of water into the hydrophilic zeolite, and the moisture is delivered from the hydrophilic zeolite through the fluid permeable shell to the treated body portion.

39 Claims, 4 Drawing Sheets

Related U.S. Application Data continuation-in-part of application No. 13/291,059, filed on Nov. 7, 2011, now Pat. No. 8,420,882, which is a continuation of application No. 10/380,803, filed as application No. PCT/US01/28908 on Sep. 17, 2001, now Pat. No. 8,524,973.

(60) Provisional application No. 60/232,826, filed on Sep. 15, 2000.

(51) Int. Cl.
  *A61L 15/44* (2006.01)
  *A61F 7/00* (2006.01)

(52) U.S. Cl.
  CPC ....... *A61L 15/44* (2013.01); *A61F 2007/0004* (2013.01); *A61F 2007/0011* (2013.01); *A61F 2007/0024* (2013.01); *A61F 2007/0203* (2013.01); *A61F 2007/0242* (2013.01); *A61F 2007/0261* (2013.01); *A61F 2013/00187* (2013.01); *A61L 2300/102* (2013.01); *A61L 2300/104* (2013.01); *A61L 2300/404* (2013.01); *A61L 2300/622* (2013.01); *A61L 2300/626* (2013.01)

(58) Field of Classification Search
  CPC ......... A61L 2300/102; A61L 2300/404; A61L 2300/622; A61L 2300/626
  See application file for complete search history.

(56) References Cited

U.S. PATENT DOCUMENTS

| | | | |
|---|---|---|---|
| 3,008,803 A | 11/1961 | Milton | |
| 3,010,789 A | 11/1961 | Milton | |
| 3,012,853 A | 12/1961 | Milton | |
| 3,013,982 A * | 12/1961 | Breck et al. | 252/181.6 |
| 3,030,181 A | 4/1962 | Milton | |
| 3,587,578 A * | 6/1971 | Walker | 604/304 |
| 4,000,028 A | 12/1976 | Hoey | |
| 4,106,478 A | 8/1978 | Higashijima | |
| 4,252,119 A * | 2/1981 | Coates | 604/306 |
| 4,273,621 A | 6/1981 | Fornoff | |
| 4,516,564 A | 5/1985 | Koiso et al. | |
| 4,525,410 A | 6/1985 | Hagiwara et al. | |
| 4,775,585 A | 10/1988 | Hagiwara et al. | |
| 4,826,497 A | 5/1989 | Marcus et al. | |
| 4,882,349 A | 11/1989 | Baglioni | |
| 4,897,297 A | 1/1990 | Zafiroglu | |
| 4,906,466 A | 3/1990 | Edwards | |
| 4,919,648 A | 4/1990 | Sibalis | |
| 4,988,053 A | 1/1991 | Choi | |
| 5,019,254 A | 5/1991 | Abrevaya et al. | |
| 5,028,435 A | 7/1991 | Katz et al. | |
| 5,123,900 A | 6/1992 | Wick | |
| 5,135,518 A | 8/1992 | Vera | |
| 5,179,944 A | 1/1993 | McSymytz | |
| 5,314,005 A | 5/1994 | Dobry | |
| RE34,692 E | 8/1994 | Becher | |
| 5,366,491 A | 11/1994 | Ingram et al. | |
| 5,409,472 A | 4/1995 | Rawlings et al. | |
| 5,413,788 A | 5/1995 | Edwards et al. | |
| 5,447,531 A | 9/1995 | Wood | |
| 5,697,961 A | 12/1997 | Kiamil | |
| H001732 H | 6/1998 | Johnson | |
| 5,846,559 A | 12/1998 | Hopp | |
| 5,890,487 A | 4/1999 | Kimmel | |
| 5,900,258 A | 5/1999 | Engler | |
| 5,935,486 A | 8/1999 | Bell et al. | |
| 5,977,428 A | 11/1999 | Bozigian et al. | |
| 5,984,995 A | 11/1999 | White | |
| 6,017,606 A | 1/2000 | Sage et al. | |
| 6,019,782 A | 2/2000 | Davis et al. | |
| 6,045,820 A | 4/2000 | Messier | |
| 6,169,223 B1 | 1/2001 | Mahr et al. | |
| 6,353,145 B1 | 3/2002 | Church | |
| 6,409,746 B1 * | 6/2002 | Igaki | A61F 7/03 607/109 |
| 6,576,004 B2 | 6/2003 | Johnston | |
| 6,592,888 B1 | 7/2003 | Jensen et al. | |
| 6,617,490 B1 | 9/2003 | Chen | |
| 6,641,264 B1 | 11/2003 | Schwebel | |
| 6,752,998 B2 | 6/2004 | Verdrel-Lahaxe et al. | |
| 6,823,860 B2 | 11/2004 | Igaki | |
| 6,874,884 B2 | 4/2005 | Schwebel | |
| 7,036,928 B2 | 5/2006 | Schwebel | |
| 7,211,070 B2 | 5/2007 | Soroudi | |
| 7,231,922 B2 | 6/2007 | Davison et al. | |
| 7,357,500 B2 | 4/2008 | Schwebel | |
| 7,513,893 B2 | 4/2009 | Soroudi | |
| 7,559,907 B2 | 7/2009 | Krempel et al. | |
| 7,652,228 B2 * | 1/2010 | Igaki | A61F 7/034 126/204 |
| 7,981,147 B2 | 7/2011 | Korb et al. | |
| 8,025,689 B2 | 9/2011 | Korb et al. | |
| 8,034,092 B2 | 10/2011 | Bruder et al. | |
| 8,114,433 B2 | 2/2012 | Huey et al. | |
| 8,202,853 B2 | 6/2012 | Adkins | |
| 8,235,954 B2 | 8/2012 | Soroudi | |
| 8,246,978 B2 | 8/2012 | Kydonieus et al. | |
| 8,261,734 B2 * | 9/2012 | Dodo | A61F 7/034 126/204 |
| 8,319,002 B2 | 11/2012 | Daniels et al. | |
| 8,333,793 B2 | 12/2012 | Igaki et al. | |
| 8,343,203 B2 | 1/2013 | Ishikawa | |
| 8,349,806 B2 | 1/2013 | Brubaker et al. | |
| 8,357,189 B2 * | 1/2013 | Ugajin | A61F 7/034 607/108 |
| 8,420,882 B2 | 4/2013 | Bruder et al. | |
| 8,430,921 B2 | 4/2013 | Wong et al. | |
| 8,506,539 B2 | 8/2013 | Guillon et al. | |
| 8,524,973 B2 * | 9/2013 | Bruder | A61F 13/00063 602/2 |
| 8,535,363 B1 | 9/2013 | Lewis | |
| 8,617,229 B2 | 12/2013 | Korb et al. | |
| 8,636,786 B2 | 1/2014 | Biser | |
| 8,642,831 B2 | 2/2014 | Larsen et al. | |
| 8,709,039 B2 | 4/2014 | Humphreys | |
| 8,747,888 B2 | 6/2014 | Kydonieus et al. | |
| 8,778,301 B2 | 7/2014 | Mamelak et al. | |
| 8,784,391 B1 | 7/2014 | Biser | |
| 8,795,718 B2 | 8/2014 | Bedard et al. | |
| 9,445,939 B2 * | 9/2016 | Bruder | A61F 13/00063 |
| 2001/0009831 A1 | 7/2001 | Schink et al. | |
| 2002/0032153 A1 | 3/2002 | Whitehouse | |
| 2002/0193026 A1 * | 12/2002 | Ota | A61F 7/02 442/261 |
| 2003/0208150 A1 | 11/2003 | Bruder et al. | |
| 2005/0022823 A1 | 2/2005 | Davison | |
| 2005/0187502 A1 | 8/2005 | Krempel | |
| 2006/0018953 A1 | 1/2006 | Guillon et al. | |
| 2007/0009583 A1 | 1/2007 | Qvist | |
| 2008/0132978 A1 | 6/2008 | Korb et al. | |
| 2008/0200885 A1 | 8/2008 | Schwebel | |
| 2008/0251085 A1 | 10/2008 | Schwebel | |
| 2009/0137533 A1 | 5/2009 | Adkins | |
| 2009/0149925 A1 * | 6/2009 | MacDonald et al. | 607/96 |
| 2009/0175926 A1 | 7/2009 | Adams | |
| 2009/0192478 A1 | 7/2009 | Soroudi | |
| 2009/0281507 A1 | 11/2009 | Humphreys | |
| 2009/0287168 A1 | 11/2009 | Mitra et al. | |
| 2009/0287282 A1 | 11/2009 | Biser et al. | |
| 2009/0287283 A1 | 11/2009 | Biser et al. | |
| 2009/0291124 A1 | 11/2009 | Bedard | |
| 2010/0010598 A1 | 1/2010 | Igaki et al. | |
| 2010/0022465 A1 | 1/2010 | Brubaker et al. | |
| 2010/0106109 A1 | 4/2010 | Bruder et al. | |
| 2010/0106111 A1 | 4/2010 | Schwebel | |
| 2010/0145469 A1 | 6/2010 | Barralet et al. | |
| 2010/0256552 A1 | 10/2010 | Korb et al. | |
| 2011/0307041 A1 | 12/2011 | Floyd | |
| 2012/0053537 A1 | 3/2012 | Bruder et al. | |
| 2012/0136285 A1 | 5/2012 | Korb et al. | |

(56) References Cited

U.S. PATENT DOCUMENTS

| | | |
|---|---|---|
| 2013/0053733 A1 | 2/2013 | Korb et al. |
| 2013/0071322 A1 | 3/2013 | Figuly |
| 2013/0131613 A1 | 5/2013 | Elkins |
| 2013/0245578 A1 | 9/2013 | Bruder et al. |
| 2013/0317459 A1 | 11/2013 | Bruder et al. |
| 2013/0317460 A1 | 11/2013 | Bruder et al. |
| 2014/0142667 A1 | 5/2014 | Biser |
| 2014/0277303 A1 | 9/2014 | Biser et al. |
| 2014/0288624 A1 | 9/2014 | Wasko |
| 2014/0330222 A1 | 11/2014 | Bruder et al. |
| 2014/0345543 A1 | 11/2014 | Saita |

FOREIGN PATENT DOCUMENTS

| | | |
|---|---|---|
| EP | 0457977 | 2/1995 |
| EP | 0691113 | 10/1996 |
| EP | 1652536 | 5/2006 |
| EP | 1328225 | 3/2010 |
| FR | 2370479 | 6/1978 |
| GB | 1315431 | 5/1973 |
| GB | 1417962 | 12/1975 |
| GB | 2228682 | 9/1990 |
| GB | 2259858 | 3/1993 |
| JP | H07112021 | 5/1995 |
| WO | 9213576 | 8/1992 |
| WO | 0178797 | 10/2001 |
| WO | 0222060 | 3/2002 |
| WO | 2014143139 | 9/2014 |

OTHER PUBLICATIONS

File History for U.S. Appl. No. 10/341,806.
File History for U.S. Appl. No. 13/291,059.
Healthcare Packaging; date unknown; 3 pages.
Healthcare Packaging; Examining Transdermal Delivery Developments; May 1, 2013; 5 pages.
Non-Patent Literture cited by EPO in Examination of EP 0691113 May 31, 1995.
Patent Owner Amended Infringement Contentions for U.S. Pat. No. 8,420,882 filed Jun. 24, 2014.
U.S. Appl. No. 60/232,826, filed Sep. 15, 2000.
U.S. Appl. No. 60/349,335, filed Jan. 14, 2002.
Zmedica—QuikClot Sport Silver; date unknown; 1 page.
International Preliminary Examination report for PCT/US01/28908 dated May 27, 2003.
International Search Report for PCT/US01/28908 dated Jan. 24, 2002.
International Search Report for PCT/US13/53221 dated Oct. 17, 2013.
Supplementary European Search Report for EP Application 01 97 3065 dated Aug. 1, 2006.
Mraz, S. 2011. "Technology helps heal chronic wounds," Machine Design, online, 5 pp., accessed Jun. 30, 2015. <http://machinedesign.com/medical/technology-helps-heal-chronic-wounds>.
"Products," Cerdak Corporation, online, accessed Jun. 30, 2015 <http://www.cerdak.co.za/Products/>.
Home page, Cerdak Corporation, online, accessed Jun. 30, 2015 <http://www.cerdak.co.za/Home/>.

* cited by examiner

MOIST HEAT THERAPY COMPRESS

CROSS REFERENCE TO RELATED APPLICATIONS

This application is a continuation of U.S. Non-Provisional patent application Ser. No. 13/832,626 filed Mar. 15, 2013, which is a continuation-in-part of U.S. Non-Provisional patent application Ser. No. 13/291,059 filed Nov. 7, 2011, which is a continuation of U.S. Non-Provisional patent application Ser. No. 10/380,803, filed May 30, 2003, which is a US. National Phase of International Patent Application Serial No. PCT/US2001/028908, filed on Sep. 17, 2001, which claims priority to and the benefit of the filing date of U.S. Patent Application No. 60/232,826, filed on Sep. 15, 2000, in the United States Patent and Trademark Office, all of which are hereby incorporated herein by reference.

FIELD OF THE INVENTION

The present invention relates generally to medical treatment devices and therapeutic methods, and more particularly to moist-heat therapy compresses and wound dressings, and to a wound dressing and/or heat-therapy compress containing antimicrobial metal(s) providing a germ and microbial free environment within the article and treated areas.

BACKGROUND

Modern wound dressings are designed to promote healing by providing a moist, warm or heated, wound environment. Warming a wound promotes healing by increasing blood flow to the area. Moisture in a wound is also very important to the healing process because it helps cells grow and divide, and reduces scarring. Available modem dressings may be dampened or moistened and then heated, for example, by microwave heating. Concurrent with the development of these dressings is the concern regarding a potential for microbial colonization of the wound. Antibiotics are available to combat infections but many people are allergic to certain antibiotics and antibiotic usage can cause gastrointestinal upset or other side effects. Further, excessive use of antibiotics has been blamed for the occurrence of treatment-resistant bacteria.

Moist heat therapy applied by an area compress may also be beneficial to the treatment of arthritic or sprained joints, strained muscles, back pain, rheumatoid arthritis, or in any treatment where heat might be applied through or to the skin to promote circulation therein and thereunder. In such applications where no wound exudates contaminate therapy materials, reusability of the compress is an attractive cost-efficient design feature. Bacterial presence can cause dermatological problems to the treated area and further, a growing microbial colony in a reusable compress can cause the spread of infection through cross-contamination when handled. This may represent a particular threat to therapy patients, many of whom have persistent or slow-healing injuries or compromised immunity systems.

A growing strategy for reducing the potential for infection or bacterial growth in a wound or on skin tissue under moist heat therapy is the incorporation of noble metal antimicrobials into the therapeutic wound dressing. The most prevalent such metal in use is silver due to its relative lack of cytotoxic effects and wide spectrum of antimicrobial effectiveness. Medical materials and instruments are available which provide the emission of silver metal or silver compounds to provide an antimicrobial effect. Such available dressings, once moistened, release silver into the surrounding liquid. The dressing thereby becomes an effective antimicrobial barrier. The silver, however, is consumed and lost in the process. Such products are inherently not conveniently reusable.

In both moist heat therapy wound dressings and compresses, bacterial and fungal growth can also cause unpleasant odor and unsightly discoloration which may adversely affect the morale of the patient. Thus there is a need in general for dressings and compresses designed to maintain sterility therein and to also provide microbial free moisture.

SUMMARY

In example embodiments, the present invention provides a wound dressing and/or therapy compress having a granular fill material permanently loaded with at least one antimicrobial agent. The at least one antimicrobial agent comprises a form of silver, which form of silver may comprise atomic silver or a composition of silver. The dressing or compress thus comprises a fluid permeable shell and a backing, each of which is attached to the other to define a plurality of fill enclosures therebetween, and a fill material enclosed within the respective enclosures. A fluid permeable outer cover may be provided to protect the dressing or compress. The dressing may be used to shelter and protect a wound while absorbing exudate, and may also provide and maintain a heated and/or moist environment to promote the healing of the wound. The compress may be used to deliver moist heat therapy to an arthritic or sprained joint or strained muscle area.

In other aspects, example embodiments of the invention relate to a wound dressing and/or therapy compress having a granular fill material such as a hydrophilic zeolite or molecular sieve material, optionally loaded with at least one metallic antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof. The dressing or compress preferably comprises a flexible and body part conformable treatment device having a fluid-permeable shell and a backing, each of which is attached to the other to define at least one, and preferably a plurality of fill enclosures therein, and a particulate fill material enclosed and loosely contained within the respective enclosure(s). A fluid-permeable removable and replaceable outer cover may optionally be provided to protect the dressing or compress.

The fill material may be prepared wet or moistened, or desiccated to dryness to either deliver or absorb moisture as appropriate to the desired treatment. The fill material absorbs or delivers this moisture through the lower shell. The shell is formed to be fluid-permeable, i.e., vapor-permeable and liquid-permeable, and is adapted to be placed in contact with a wound or tissue directly or through a vapor-permeable and liquid-permeable outer cover. The backing may also be fluid-permeable, or non-permeable if so desired, so as to allow for the release or retention of moisture as appropriate to the desired treatment.

The shell and backing are joined to form at least one, and preferably a plurality of enclosures there between. The enclosures may contain the loaded fill material. The presence of the antimicrobial agent within all or some of the fill material promotes a germ and microbial free environment at and near the lower shell and within the dressing or compress.

The device and its constituent components are preferably water resistant and microwave safe, whereby the device can safely be subjected to repeated cycles of wetting, microwave heating and cooling, without significant deterioration or loss of its moist heat therapy, antimicrobial or antibacterial characteristics. The dressing or compress may be washable and reusable.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
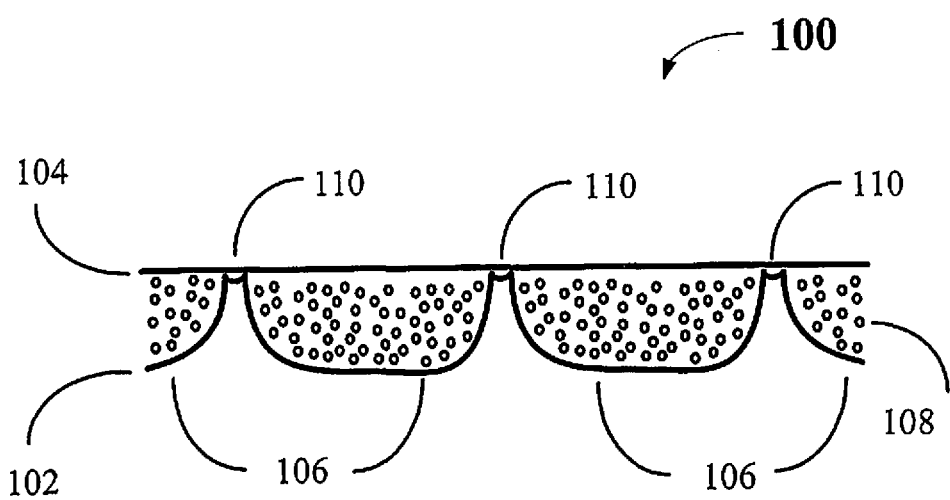
FIG. 1 is a partial side cross-sectional view of a dressing or compress according to an example embodiment of the present invention.

Referring now to FIGS. 1-4, and as best illustrated in FIG. 1, a dressing or compress 100 is illustrated having a lower shell 102 and a flexible upper backing 104 which are joined or otherwise fastened to one another to form a series of enclosures 106 there between. The enclosures are provided for the containment and relatively uniform distribution of a plurality of fill granules 108 placed therein. The enclosures may be fashioned as filled pods which are draped from the backing. The shell 102 forms the contact surface of the dressing or compress used to drape or form the bottom of the filled enclosures which are to be placed against the tissue to be treated, and to conform to the shape of the treatment area. The backing forms the smoother outer surface of the dressing or compress facing away from the treatment area.

Figure 2:
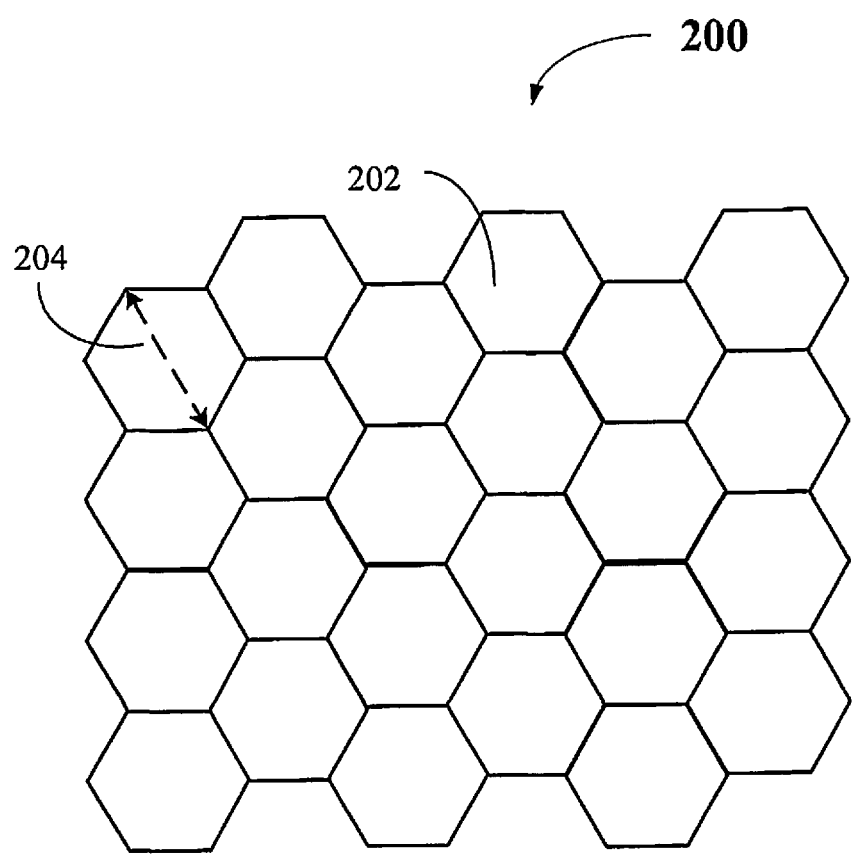
FIG. 2 is partial plan view of an exemplary hexagonal enclosure pattern according to an example embodiment of the present invention.

The enclosures 106 may be defined as hexagons using patterned seams 110 for local symmetry and efficient regular plane division. An illustrative hexagonal pattern 200 of enclosures 202 is illustrated in FIG. 2. The enclosures might also be fashioned as circles, octagons, or of any desired shape as may be appropriated for the desired treatment. The enclosures may be selectively sized as appropriate to the application. Each hexagonal shaped enclosure 202 has a lengthwise dimension 204 extending from a first corner to an opposite second corner thereof. For example, and not by way of limitation, this dimension may be in the range of from approximately one inch to approximately four inches in length. Large treatment areas such as the human torso or appendages may best be served with enclosures having a dimension 204 extending lengthwise for approximately 4 inches. Highly contoured areas such as the face may best be served with enclosures having a dimension 204 of approximately 1 inch in length.

Figure 3:
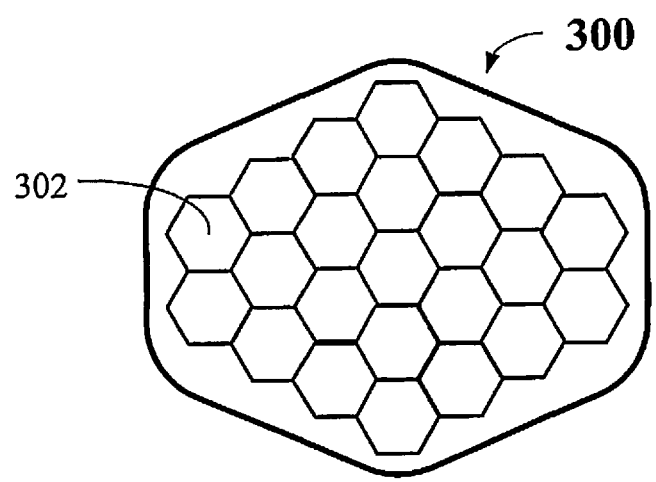
FIG. 3 is a plan view of an alternate exemplary dressing or compress with a hexagonal enclosure pattern.
Figure 4:
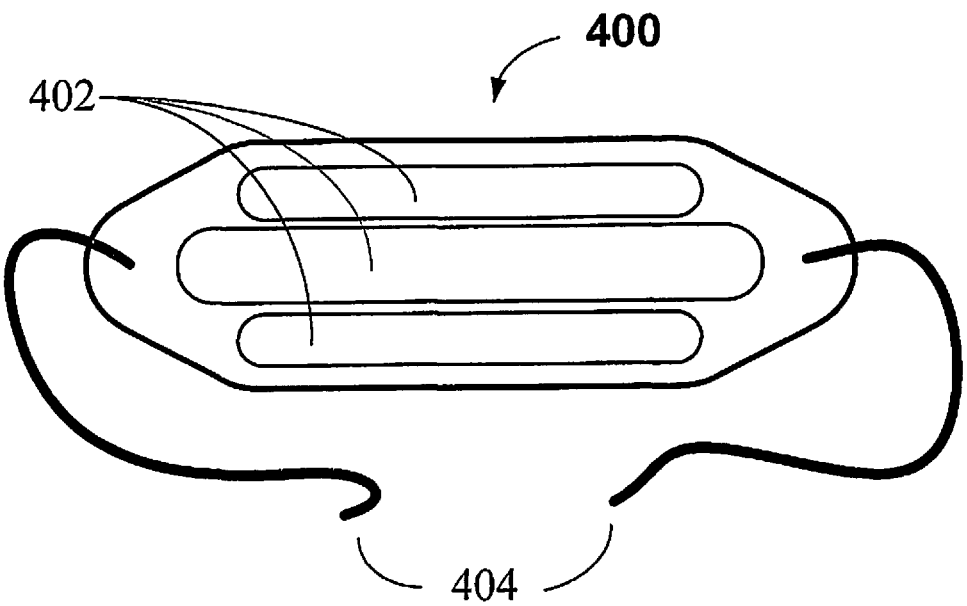
FIG. 4 is a plan view of a wrap compress with ties using the dressing or compress of the present invention.
Figure 5:
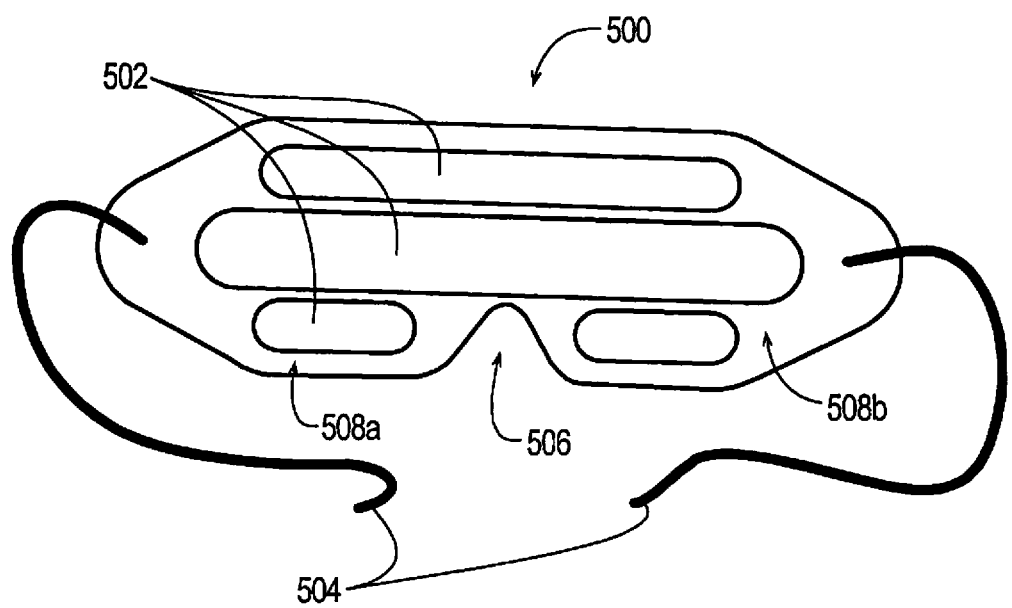
FIG. 5 is a plan view of a moist heat therapy compress in the form of an eye or nasal/sinus compress according to another example embodiment of the present invention.

An alternate dressing or compress 300 is illustrated in FIG. 3, having a plurality of hexagonal patterned enclosures 302. Each of the enclosures may also be formed as a channel-like rectangle, as illustrated in FIG. 4. The embodiment of the dressing or compress 400 is formed to have several channel enclosures 402 formed within a wrap compress having securing ties 404. So constructed, the dressing or compress 400 may be provided for the treatment of soreness or strains of the human back. In alternative applications, for example as illustrated in FIG. 5, the dressing or compress 500 is adapted for use as an eye compress for application of moist heat therapy to a subject's eyes with enclosures 502 for containing the fill granules and securing ties 504 for attachment around a patient's head, such as for treatment of dry-eye or other eye conditions; for moist heat therapy to a subject's sinus or nasal areas; and/or for treatment of other body parts of a human or animal subject or patient for wound care, epitheliazation, antibacterial, antimicrobial, antiviral, antifungal, anti-inflammatory, analgesic, moist heat therapy and/or other treatment purposes. In the eye compress configuration shown in FIG. 5, the flexible outer shell includes a generally triangular or trapezoidal nose cut-out area 506 at a medial portion of its lower edge, between first and second lobes 508a, 508b for covering areas over and around the user's left and right eyes when in use, with the ties or an elastic strap placed around the user's head, typically over the ears, to retain the compress 500 in place.

The size of the enclosures and overall dressing are selected to serve the desired treatment. Selected single sites for treatment such as the eye may best be treated using a single enclosure dressing or compress appropriately sized and shaped to rest comfortably in the eye hollow of the human face. The dressing or compress may be shaped as a regular or irregular polygon, any smooth closed curve, or any closed combination of line segments and smooth curves. The invention is not limited to constructions conforming to or only serving the human body. The invention provides a potentially useful treatment for the ailments of mammals and any animals benefiting from the healing properties of moisture and/or heat therapy.

A fluid-permeable, i.e., a vapor-permeable and/or a liquid-permeable protective outer cover (not illustrated) may be provided to encompass the compress. This may be preferable to limit contamination of the dressing or compress. For the treatment of open wounds, an uncovered disposable dressing (not illustrated) may be preferred for optimal formable contact with, and healing of, the exposed tissues. Alternatively, the cover and other materials of the compress or dressing are washable for repeated re-use.

The fill contained within the enclosure or enclosures may comprise a synthetic porous crystalline granular aluminosilicate zeolite, commonly used as a molecular sieve material, or other substances with similar properties. The fill material may further comprise other inert additives and physical matrices without affecting the antimicrobial and hydrous efficacies of the fill. Optionally, the wound dressing and/or therapy compress comprises a granular fill material such as a hydrophilic zeolite or molecular sieve material, with at least one metallic antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof deposited therein. For example, silver or other metal loading of the fill may be attained by the process of ion-exchange, as known. In this process, a solution containing atomic silver or a composition of silver bathes, or is passed through, a bed of the fill granules 108 (FIG. 1). An ion-exchange column method, as known in the art, may be performed in which an aqueous solution containing atomic silver or a composition of silver may be passed through a column bed of the fill granules, and the eluted solution may again be passed through the bed or may receive additional silver and then be again passed through the bed.

Various ion-exchange schedules known in the art may be applied to produce retention of the silver or other metals. For example, the final content by weight of the atomic silver or silver composition may be as high as twenty percent of the final loaded fill granules. The loaded fill granules produced by ion-exchange will exhibit high retention of the silver or other metals even under subsequent exposure to fluids and microwave irradiation. The fill granules may comprise a blend of both loaded and unloaded zeolite or a substance retaining silver or other metals. The presence of the atomic silver or other metals will not interfere with the useful properties of the fill granules such as the moisture desorption and adsorption properties which may be desirable in the use of the dressing or compress. The inherent hydrophilic nature of the zeolite provides that a substantial water content is available therein by absorption from the atmosphere. The water so absorbed may be sufficient, or may be supplemented by manually added water, for providing the microwave responsive water content of the dressing or compress. The compositions of silver or other metals used may include but are not limited to, metal compounds, and metal salts such as silver chloride and silver nitrate.

The presence of the silver or other metals within the fill granules contained in the enclosure of the invention provides anti-microbial properties to the dressing or compress. The ion-exchange loaded fill granules will retain the silver or other metals despite microwave heating as may be required in the use of the dressing or compress, which prevents the release of silver or other metals into a treated wound if the invention is used as a dressing. Further, the retention of the silver or other metals within the fill granules provides assured antimicrobial performance in a reusable and potentially washable, if so desired, moist heat therapy compress.

The compress or dressing of the present invention alternatively comprises fill granules such as a hydrophilic zeolite with or without anti-microbial metal(s) disposed therein. For wound dressing applications, the provision of anti-microbial metal(s) may be preferable. For therapeutic compress applications, the provision of anti-microbial metal(s) is optional. Moist heat therapy applied by an area compress may be beneficial to the treatment of arthritic or sprained joints, strained muscles, back pain, rheumatoid arthritis, or in any treatment where heat might be applied through or to the skin of a human or animal patient or subject, to promote circulation therein and there under. In such applications where no wound exudates contaminate (imbedded metals may not be incorporated into the molecular sieve granules when used for this purpose), reusability and ability to wash the compress are attractive cost-efficient design features. Thus, example embodiments of the invention comprise a washable and/or reusable compress.

In the described embodiments of the invention, the lower shell and the upper backing are each constructed of materials known in the art. Each may therefore be comprised of multilayered laminates, for example, with pore sizes selectable to meet the moisture transmission and retention properties desired for the specific treatment sought. The dressing or compress is adapted to be placed and to remain in intimate contact with the area to be treated to maintain a heated and/or moist environment thereabout. Dressing or compress constructions using woven textiles of natural fibers have been found to have limited spatial conformance to the various shapes, dimples, wrinkles and joints offered by the human body, although these materials may be used if so desired.

Accordingly, preferred dressing or compress constructions will use formable woven and non-woven synthetic materials or combinations thereof which may include, but are not limited to, synthetic olefin, polyester, urethane, and nylon. The shell and the backing may be fastened together across the area of the dressing or compress with a fill material, the fill granules 108, received there between. The shell and the backing may be fastened to one another by methods which may include, but are not limited to, adhesive attachment, RF welding, ultra-sonic attachment, sewing, or patterned heat application using a template or forming die to form a seal. To provide for the secure placement of the dressing or compress, peripheral or attachment fastening devices may be included which may comprise the desired number of Velcro®-type fasteners, adhesives, high tactility polymer materials, and/or material ties.

Throughout the construction of the dressing or compress, attention and care is taken in the selection of materials regarding thermal response to microwave heating. For design simplicity, all synthetic, microwave non-responsive materials may be selected to provide that the fill and/or water content of a moistened dressing or compress provide the only substantial thermal response to microwave irradiation.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention. The words "a," "an," or "the" can mean one or more, depending upon the context in which the words are used hereinabove.

What is claimed is:

1. A therapeutic compress for moist heat therapy treatment of a treated body part of a human or animal patient by application of the compress to the treated body part and transfer of moist heat to the treated body part, the compress comprising:
   a flexible outer shell for application to the treated body part of the patient, the outer shell forming at least one enclosure, and being microwave compatible for repeated microwave heating, the flexible outer shell being transmissive of moist heat from within the at least one enclosure through the flexible outer shell to the treated body part to which the compress is applied;
   a plurality of fill granules loosely contained within the at least one enclosure, wherein the plurality of fill granules consist essentially of hydrophilic zeolite particles for retaining moist heat and delivery of moist heat from the hydrophilic zeolite fill granules through the flexible outer shell to provide moist heat therapy to the treated body part of the patient, wherein the hydrophilic zeolite fill granules allow repeated absorption and dissipation of moisture and heat to and from the hydrophilic zeolite fill granules for repeated therapeutic deliveries of moist heat therapy from the compress to the treated body part of the patient.

2. The therapeutic compress of claim 1, wherein the treated body part of the patient is an eye, and the compress is configured as an eye compress for treatment of the eye.

3. The therapeutic compress of claim 2, wherein the flexible outer shell comprises first and second lobes, each for application over a respective left and right eye region of the patient, and a nose cut-out region between the first and second lobes.

4. The therapeutic compress of claim 1, wherein the hydrophilic zeolite fill granules comprise an antimicrobial metal retained therein.

5. The therapeutic compress of claim 4, wherein the antimicrobial metal is selected from silver, copper, copper oxide, gold, magnesium oxide, aluminum oxide, titanium dioxide, zinc oxide, cobalt, nickel, zirconium, molybdenum, tin, lead, metal oxides, metal ions, metal particles or nanoparticles, and alloys, mixtures and combinations thereof.

6. The therapeutic compress of claim 1, wherein the outer shell comprises a synthetic fabric selected from synthetic olefin, polyester, urethane, nylon, and combinations thereof.

7. The therapeutic compress of claim 1, wherein the at least one enclosure defines a geometric shape selected from a hexagon, a circle, an ellipse, a channel, and a polygon.

8. The therapeutic compress of claim 1, wherein the flexible outer shell is washable.

9. The therapeutic compress of claim 1, wherein the treated body part of the patient is a human back, and the compress is configured as a moist heat back wrap.

10. A moist heat back wrap for therapeutic treatment of a human subject's back by application of the back wrap to the human subject's back to deliver moist heat to at least a portion of the back, the moist heat back wrap comprising:
    a flexible outer shell configured for application to the human subject's back, the outer shell forming at least one enclosure, and being microwave compatible for repeated microwave heating, the flexible outer shell being transmissive of moist heat from within the at least one enclosure through the flexible outer shell to the human subject's back to which the compress is applied;
    a plurality of fill granules loosely contained within the at least one enclosure, wherein the plurality of fill granules consist essentially of hydrophilic zeolite particles for retaining moist heat and delivery of moist heat from the hydrophilic zeolite fill granules through the flexible outer shell to provide moist heat therapy to the human subject's back, wherein the hydrophilic zeolite fill granules allow repeated absorption and dissipation of moisture and heat to and from the hydrophilic zeolite fill granules for repeated therapeutic deliveries of moist heat therapy from the compress to the human subject's back.

11. The moist heat back wrap of claim 10, wherein the hydrophilic zeolite fill granules comprise an antimicrobial metal retained therein.

12. The moist heat back wrap of claim 11, wherein the antimicrobial metal is selected from silver, copper, copper oxide, gold, magnesium oxide, aluminum oxide, titanium dioxide, zinc oxide, cobalt, nickel, zirconium, molybdenum, tin, lead, metal oxides, metal ions, metal particles or nanoparticles, and alloys, mixtures and combinations thereof.

13. The moist heat back wrap of claim 10, wherein the outer shell comprises a synthetic fabric selected from synthetic olefin, polyester, urethane, nylon, and combinations thereof.

14. The moist heat back wrap of claim 10, wherein the at least one enclosure defines a geometric shape selected from a hexagon, a circle, an ellipse, a channel, and a polygon.

15. The moist heat back wrap of claim 10, wherein the flexible outer shell is washable.

16. A moist heat wrap for therapeutic treatment of a body part of a human subject by application of the wrap to the body part to deliver moist heat to the body part, the moist heat wrap comprising:
    a flexible outer shell configured for application to the body part, the outer shell forming at least one enclosure, and being microwave compatible for repeated microwave heating, the flexible outer shell being transmissive of moist heat from within the at least one enclosure through the flexible outer shell to the body part to which the compress is applied;
    a plurality of fill granules loosely contained within the at least one enclosure, wherein the plurality of fill granules consist essentially of hydrophilic zeolite particles for retaining moist heat and delivery of moist heat from the hydrophilic zeolite fill granules through the flexible outer shell to provide moist heat therapy to the body part, wherein the hydrophilic zeolite fill granules allow repeated absorption and dissipation of moisture and heat to and from the hydrophilic zeolite fill granules for repeated therapeutic deliveries of moist heat therapy from the compress to the body part.

17. The moist neck wrap of claim 16, wherein the hydrophilic zeolite fill granules comprise an antimicrobial metal retained therein.

18. The moist heat wrap of claim 17, wherein the antimicrobial metal is selected from silver, copper, copper oxide, gold, magnesium oxide, aluminum oxide, titanium dioxide, zinc oxide, cobalt, nickel, zirconium, molybdenum, tin, lead, metal oxides, metal ions, metal particles or nanoparticles, and alloys, mixtures and combinations thereof.

19. The moist heat wrap of claim 16, wherein the outer shell comprises a synthetic fabric selected from synthetic olefin, polyester, urethane, nylon, and combinations thereof.

20. The moist heat wrap of claim 16, wherein the at least one enclosure defines a geometric shape selected from a hexagon, a circle, an ellipse, a channel, and a polygon.

21. The moist heat wrap of claim 16, wherein the flexible outer shell is washable.

22. A moist heat wrap article for delivery of moist heat therapy to a treatment area of a human body, the article comprising:
a moist heat permeable shell for application to the treatment area by wrapping the shell about a portion of the human body, the shell forming a plurality of enclosures defining elongate channels extending generally parallel to one another; and
a plurality of fill granules loosely contained within each of the plurality of enclosures defining elongate channels, the fill granules being moisture
absorptive and releasing said moisture upon heating for delivering moist heat from the fill granules through the moist heat permeable shell to the treatment area, the fill granules consisting essentially of hydrophilic zeolite particles; and
at least one attachment strap attached to the shell and comprising a hook-and-loop fastener material for securing the shell in place wrapped about the portion of the human body at the treatment area.

23. The article of claim 22, wherein the hydrophilic zeolite granules are configured to allow repeated absorption and dissipation of moisture to and from the hydrophilic zeolite material.

24. The article of claim 22, wherein the shell comprises a synthetic microwave non-responsive fabric.

25. The article of claim 22, wherein the shell is fluid permeable.

26. The article of claim 22, wherein the shell and the plurality of fill granules are configured to be reused after washing.

27. The article of claim 22, wherein at least a portion of the hydrophilic zeolite fill granules are antimicrobial, comprising up to twenty percent weight content of silver.

28. The article of claim 27, wherein the silver comprises at least one of the group comprising atomic silver, silver compounds, silver salts, silver chloride, and silver nitrate.

29. The article of claim 27, wherein the fill granules comprise silver-loaded zeolite granules and unloaded zeolite granules.

30. A moist heat back wrap for delivery of moist heat to a back body portion of a human subject, the moist heat back wrap comprising:
a moist heat permeable shell configured for application to the back body portion by wrapping at least partially about a torso of the human subject, the shell comprising a plurality of enclosures defining channels extending generally parallel to one another;
a plurality of fill granules loosely contained within the plurality of enclosures defining channels for delivering moist heat from the fill granules through the moist heat permeable shell to the back of the human subject, the fill granules consisting essentially of hydrophilic zeolite particles; and
at least one attachment strap extending from the shell and comprising a hook-and-loop fastener material for securing the shell in place on the back body portion and wrapped at least partially about the torso of the human subject.

31. The back wrap of claim 30, wherein the hydrophilic zeolite particles are configured to allow repeated absorption and dissipation of moisture.

32. The back wrap of claim 30, wherein the flexible backing and shell comprises a synthetic microwave non-responsive fabric.

33. The back wrap of claim 30, wherein the shell is fluid permeable.

34. The back wrap of claim 30, wherein the shell and the plurality of fill granules are configured to be reused after washing.

35. The back wrap of claim 30, wherein at least a portion of the hydrophilic zeolite particles are antimicrobial, comprising up to twenty percent weight content of silver.

36. The back wrap of claim 35, wherein the silver comprises at least one selected from the group comprising atomic silver, silver compounds, silver salts, silver chloride, and silver nitrate.

37. The back wrap of claim 35, wherein the hydrophilic zeolite particles comprise silver-loaded zeolite particles and unloaded zeolite particles.

38. A moist heat back wrap for delivery of moist heat therapy to a human subject's back, the back wrap comprising a moist heat permeable shell comprising a plurality of enclosures, the enclosures defining generally rectangular channels filled with particles loosely contained therein, wherein the particles consist essentially of hydrophilic zeolite particles, and having attachment straps extending from opposite sides of the shell, the straps comprising hook-and-loop fastener material for securing the back wrap to the human subject's back for delivery of moist heat therapy thereto.

39. A therapeutic compress for moist heat therapy treatment of a treated body part of a human or animal patient by application of the compress to the treated body part and transfer of moist heat to the treated body part, the compress comprising:
a flexible outer shell for application to the treated body part of the patient, the outer shell forming at least one enclosure, and being microwave compatible for repeated microwave heating, the flexible outer shell being transmissive of moist heat from within the at least one enclosure through the flexible outer shell to the treated body part to which the compress is applied;
a plurality of hydrophilic zeolite fill granules loosely contained within the at least one enclosure for retaining moist heat and delivery of moist heat from the hydrophilic zeolite fill granules through the flexible outer shell to provide moist heat therapy to the treated body part of the patient, wherein the hydrophilic zeolite fill granules allow repeated absorption and dissipation of moisture and heat to and from the hydrophilic zeolite fill granules for repeated therapeutic deliveries of moist heat therapy from the compress to the treated body part of the patient;
wherein the treated body part of the patient is a human back, and the compress is configured as a moist heat back wrap.

* * * * *